United States Patent [19]

Drell

[11] Patent Number: 5,023,083

[45] Date of Patent: Jun. 11, 1991

[54] AZARBINE COMPOSITION

[76] Inventor: William Drell, 4566 Sherlock Crt., San Diego, Calif. 92122

[21] Appl. No.: 464,598

[22] Filed: Jan. 12, 1990

Related U.S. Application Data

[63] Continuation of Ser. No. 100,034, Sep. 23, 1987, abandoned.

[51] Int. Cl.$^5$ ................................................ A61K 9/36
[52] U.S. Cl. ..................................... 424/439; 424/459;
424/460; 424/461; 424/462; 424/463; 424/475;
424/476; 424/477; 424/478; 424/479; 424/480;
424/481; 424/482
[58] Field of Search ............... 424/439, 459, 460, 461,
424/462, 463, 475, 476, 477, 478, 479, 480, 481,
482

[56] References Cited

PUBLICATIONS

CA88(23): 163706r.
CA89(20): 168986n.
CA106(25); 207689j.

*Primary Examiner*—John Kight, III.
*Assistant Examiner*—Frederick Krass
*Attorney, Agent, or Firm*—Christie, Parker & Hale

[57] ABSTRACT

A method for treating azaribine-responsive diseases in patient's who exhibit severe pyridoxal phosphate depletion following the oral administration of azaribine comprises first encapsulating azaribine in a film-forming substance which is selectively soluble in the digestive juice of the intestines. The encapsulated azaribine is then orally administered to the patient in an amount effective for the treatment of the disease, preferably in an amount to provide from about 1.5 to about 15 grams of azaribine per square meter of patient body surface area per day.

32 Claims, No Drawings

AZARBINE COMPOSITION

CROSS-REFERENCE TO RELATED APPLICATIONS

This is a continuation of application Ser. No. 07/100,034, filed Sept. 23, 1987, abandoned.

FIELD OF THE INVENTION

This invention relates to the treatment of azaribine-responsive diseases and more particularly to the treatment of azaribine-responsive diseases in patients exhibiting severe pyridoxal phosphate deficiency following the oral administration of azaribine.

BACKGROUND OF THE INVENTION

Azaribine (2', 3', 5'-triacetate-6-azauridine) has been found to be effective in oral dosage form for the treatment of psoriasis, psoriatic arthritis, polycythemia vera, mycosis fungoides, and choriocarcinoma. However, a severe side effect, namely life-threatening thromboembolic episodes of up to four percent of the patients treated, caused the recall of the drug by the Food and Drug Administration (FDA).

It has been discovered in man, as well as in rabbits, that oral administration of the azaribine resulted in severe pyridoxal phosphate deficiency and abnormally high levels of homocysteine, which are presumed to be related to the thrombogenic side-effects of this drug. It has also been shown that, in rabbits, severe pyridoxal phosphate deficiency, as well as the homocysteinemia, can be prevented or at least reduced by the concomitant administration of pyridoxine.

The mechanism by which azaribine interferes with pyridoxal phosphate is unknown, but has been attributed to an interference with pyridoxal phosphate coenzymes essential to the proper metabolism of the accumulated amino acids. It has been shown that homocysteine accumulates in pigs fed a vitamin $B_6$-deficient diet. It has been suggested that a catabolite of 6-azauridine, the active drug substance formed by the hydrolysis of azaribine after its absorption, results through cleavage of the triazine ring of 6-azauridine. This catabolite has been postulated to be a hydrazine or semicarbazide derivative which can readily and rapidly react with pyridoxal phosphate, resulting in severe deficiency.

SUMMARY OF THE INVENTION

It has been discovered that, when azaribine is administered in a formulation which is resistent to absorption by the stomach, severe pyridoxal phosphate depletion and homocysteinemia do not develop. Accordingly, the present invention provides a chemical formulation and a method for the treatment of azaribine-responsive diseases, including psoriasis, psoriatic arthritis, polycythemia vera, mycosis fungoides and choriocarcinoma, in patients that exhibit severe pyridoxal phosphate depletion following the oral administration of azaribine.

The chemical formulation comprises a generally solid composition containing azaribine which has been encapsulated in an enteric coating i.e., a film-forming substance which is selectively soluble in the digestive juice of the intestine. The formulation may be orally administered in tablet, capsule or any other suitable form.

Preferably, the composition further comprises a pyridoxine compound selected from pyridoxine, pyridoxal phosphate, pyridoxamine, pyridoxamine phosphate, pyridoxal, pyridoxine phosphate and mixtures thereof. The pyridoxine compound is preferably present in an amount sufficient to supply at least about 0.0005 mole, preferably at least about 0.001 mole, and more preferably 0.025 mole of the pyridoxine compound per mole of the administered azaribine.

The method of treatment comprises first encapsulating azaribine in an enteric coating. The coated azaribine is then orally administered to a patient that exhibits severe pyridoxal phosphate deficiency following the oral administration of uncoated azaribine in an amount effective for the treatment of the disease. Preferably the azaribine is administered in an amount sufficient to provide from about 1.5 to about 15 grams of azaribine per square meter of body surface area per day, preferably in two or more equal doses.

The method preferably further comprises the administration of a pyridoxine compound, which is administered within 24 hours before or after the administration of the azaribine and preferably administered simultaneously with the azaribine. The pyridoxal phosphate is administered in an amount sufficient to supply at least 0.0005 mole, preferably at least about 0.001 mole, more preferably at least about 0.025 mole of the pyridoxine compound per mole of the administered azaribine.

DETAILED DESCRIPTION

In accordance to the present invention, there is provided a chemical formulation useful in treating mammals having azaribine-treatable diseases, i.e., diseases responsive to the administration of azaribine, who exhibit severe pyridoxal phosphate depletion following the oral administration of azaribine. Azaribine-treatable diseases which may be mentioned include psoriasis, psoriatic arthritis, polycythemia vera, mycosis fungoides and choriocarcinoma.

The chemical formulation comprises a generally solid composition containing azaribine which is encapsulated in an enteric coating. As used herein, "azaribine" means 6-azauridine triacetate, or 2', 3', 5'-triacetyl-6-azauridine.

Preferably, the composition comprises azaribine, in powder form, that has been applied to a carrier substrate, such as sugar beads, or the like. Application may be by any conventional method. An enteric coating is then applied to the azaribine-coated substrate to encapsulate the substrate and azaribine.

The enteric coating may be made of any suitable composition. Suitable enteric coatings are described, for example, in U.S. Patent Nos. 4,311,833 to Namikoshi, et al.; 4,377,568 to Chopra; 4,385,078 tO Onda, et al.; 4,457,907 to Porter; 4,462,839 to McGinley, et al.; 4,518,433 to McGinley, et al.; 4,556,552 to Porter, et al.; 4,606,909 to Bechgaard, et al.; 4,615,885 to Nakagame, et al.; and 4,670,287 to Tsuji, all of which are incorporated herein by reference.

Preferred enteric coating compositions include alkyl and hydroxyalkyl celluloses and their aliphatic esters, e.g., methylcellulose, ethylcellulose, hydroxyethylcellulose, hydroxypropylcellulose, hydroxybutylcellulose, hydroxyethylethylcellulose, hydroxyprophymethylcellulose, hydroxybutylmethyl-cellulose, hydroxypropylcellulose phthalate, hydroxypropylmethylcellulose phthalate and hydroxypropylmethylcellulose acetate succinate; carboxyalkylcelluloses and their salts, e.g., carboxymethylethylcellulose; cellulose acetate phthalate; polycarboxymethylene and its salts and derivatives; polyvinylalcohol and its esters, polycaboxymethylene copolymer with sodium formaldehyde carboxylate; acrylic polymers and copolymers, e.g., methacrylic acid-methyl methacrylic acid copolymer and methacrylic acid-methyl acrylate copolymer; edible oils such as peanut oil, palm oil, olive oil and hydrogenated vegetable oils; polyvinylpyrrolidone; polyethyleneglycol and its esters, e.g., and natural products such as shellac.

Other preferred enteric coatings include polyvinyacetate esters, e.g., polyvinyl acetate phthalate; alkyleneglycolether esters of copolymers such as partial ethylene glycol monomethylether ester of ethylacrylate-maleic anhydride copolymer or diethyleneglycol monomethylether ester of methylacrylate-maleic anhydride copolymer, N-butylacrylate-maleic anhydride copolymer, isobutylacrylate-maleic anhydride copolymer or ethylacrylate-maleic anhydride copolymer; and polypeptides resistant to degradation in the gastric environment, e.g., polyarginine and polylysine.

Mixtures of two or more of the above compounds may be used as desired. The presently preferred enteric coating comprises cellulose acetate phthalate.

The enteric coating material may be mixed with various excipients including plasticizers such as triethyl citrate, acetyl triethyl citrate, diethyl phthalate, dibutyl phthalate, dibutyl sebacate, dibutyl tartrate, dibutyl maleate, dibutyl succinate and diethyl succinate and inert fillers such as chalk or pigments.

The composition and thickness of the entire coating may be selected to dissolve immediately upon coated with the digestive juice of the intestine. Alternatively, the composition and thickness of the anterior coating may be selected to be a time-release coating which dissolves over a selected period of time, as is well known in the art.

A particularly preferred composition is made by first moistening nu-pariel sugar beads with an alcohol, preferably having two to eight carbon atoms. The alcohol can be primary, secondary or tertiary. A layer of azaribine, for example about 3 microns thick, is then dusted onto the beads. The treated beads are again moistened with an alcohol and azaribine is again dusted onto the moistened beads. This procedure is repeated until the desired total weight of the beads is achieved. A total weight of approximately four times the weight of the original nu-pariel beads is presently preferred. The beads are then moistened with pharmaceutical or confectioner's shellac, for example, about 0.1 to about 0.5 parts of confectioner's shellac Number 4, or the like, at a temperature of from about 40 to about 60° C. The beads are allowed to partially dry until tacky.

Then, a conventional enteric coating dissolved in alcohol, alcohol water or alcohol solvent at a concentration ranging from about 0.1 to about 40.0% is then sprayed onto the beads. The amount of enteric coating depends on the particular enteric coating composition used and is preferably sufficient to substantially prevent the absorption of azaribine in the stomach. An amount approximately one-sixth the amount of the shellac is presently preferred.

Hydroxyalkyl celluloses and their aliphatic esters, carboxyalkyl celluloses and their salts, polycarboxymethylene and its salts and derivatives, polyvinyl alcohol and its esters, polycarboxy methylene copolymer with sodium formaldehyde carboxylates, poly-vinylpyrrolidone, and polyethylene glycol and its esters can be applied as enteric coatings by first dissolving the compound in a minimum amount of water. Alcohol is then added to the point of incipient cloudiness. The mixture can then be applied by conventional techniques.

Application of cellulose acetate phthalate may be accomplished by simply dissolving the cellulose acetate phthalate in a minimum amount of alcohol and then applying by conventional techniques. Hydrogenated vegetable oils may be applied by first dissolving the oil in a minimal amount of a non-polymer solvent, such as methylene chloride, chloroform or carbon tetrachloride, then adding alcohol to the point of incipient cloudiness and then applying by conventional techniques.

According to the method of invention, azaribine is first encapsulated in an enteric coating, for example, as described above. The coated azaribine is then administered orally to a patient that exhibits severe pyridoxal phosphate deficiency following the oral administration of azaribine not having an enteric coating.

To be effective in the treatment of psoriasis, psoriatic arthritis, polycythemia vera, mycosis fungoides and choriocarcinoma, azaribine is preferably administered in a dosage of from about 1.5 grams to about 15 grams, and preferably about 4.5 grams of azaribine per square meter of body surface area per day. This amount provides from about gram to about 10 grams, and preferably about 3 grams, of free 6-azauridine, the active substance formed by the deacetylation of azaribine during or after its absorption into the blood stream.

The mechanism by which application of an enteric coating prevents severe pyridoxal phosphate deficiency is not completely understood. While not being bound by theory, it is believed that catabolites of the azauridine compound may be responsible for the depletion of a serum pyridoxal levels. Since most of the drug and its metabolites are excreted in the urine within six hours after administration, the initial dramatic decrease in the levels of pyridoxal phosphate in the serum possibly could be explained by its binding to a rapidly formed catabolite. It is presumed then, that the enteric coating prevents or at least reduces the formation of the catabolite. While the mechanism is not clear, some of the advantages are. Oral administration of azaribine has proven useful in the treatment of certain diseases, but cannot be used with patients that tend to exhibit severe decrease in serum of pyridoxal phosphate levels. The presence of the enteric coating reduces, if not eliminates, this problem allowing azaribine to be used with those patients.

It has been shown that the concomitant administration of a pyridoxine compound with the administration of azaribine will compensate, at least partially, if not wholly, for the reduction in serum pyridoxal phosphate levels caused by the administration of azaribine. Accordingly, the azaribine formulation of the present invention preferably comprises a pyridoxine compound. This provides two separate mechanisms by which the administration of azaribine is made safer. First, the enteric coating substantially prevents severe rapid reduction in serum pyridoxine phosphate levels. Secondly, if, for some reason, the level of serum pyridoxine phosphate should decrease, the administered pyridoxine compound will compensate for the decrease.

The pyridoxine compound is preferably selected from the group consisting of pyridoxine, pyridoxal phosphate, pyridoxamine, pyridoxamine phosphate, pyridoxal, pyridoxine phosphate, pyridoxine hydrochloride and mixtures thereof. The presently preferred pyridoxine compound is pyridoxine as the hydrochloride salt.

The amount of the pyridoxine compound is not critical but is preferably sufficient to provide at least about 0.0005 mole and more preferably at least about 0.001 mole and even more preferably at least about 0.025 mole of the pyridoxine compound per mole of the azaribine. The preferred mole ratio of the pyridoxine compound to the azaribine is at least about 1:2,000, preferably about 1:1,000 and more preferably about 1:40.

The pyridoxine compound may be administered as part of the azaribine in the form of a pill or capsule or a powder. Additionally, the pyridoxine compound may be administered separately from the azaribine formulation and administered as a pill, capsule, powder or even as a liquid. If administered separately, the pyridoxine compound is preferably administered within 24 hours, before or after the administration of the azaribine compound. It is presently preferred to combine the pyridoxine compound and the enteric azaribine formulation in a single tablet or capsule to assure that a patient is assured of the benefit of both compositions.

EXAMPLE 1

An enteric azaribine formulation was prepared according to the following procedure. 125 mg. of nupariel beads were moistened with ethanol in a pharmaceutical coating pan. Azaribine was dusted onto the beads to form a layer approximately 3 microns thick. The beads were again moistened with ethanol and dusted with azaribine. The procedure was repeated until about 475 mg. of azaribine had been applied to the beads. The beads were then moistened with approximately 70 mg. confectioner's shellac No. 4 at a temperature of about 50° C. The beads were allowed to dry until tacky. Approximately 12 mg. of cellulose acetate phthalate dissolved in ethanol was then sprayed onto the beads and allowed to dry.

The preceding description has been presented with reference to presently preferred embodiments of the invention. Workers skilled in the art and technology to which this invention pertains will appreciate that alterations and changes in the described compositions and procedures can be practiced without meaningfully departing from the principles, spirit and scope of this invention.

Accordingly, the foregoing description should not be read as pertaining only to the precise compositions and procedures described, but rather should be read consistent with and as support for the following claims which are to have their fullest fair scope.

What is claimed is:

1. A method for treating azaribine-responsive diseases in animals that exhibit severe serum pyridoxal phosphate depletion following oral administration of azaribine comprising:
   encapsulating azaribine in a film-forming substance which is selectively soluble in the digestive juice of the intestine; and
   orally administering the encapsulated azaribine to the animal.

2. A method as claimed in claim 1 wherein the film-forming substance forms a time-release coating which dissolves in the digestive juice of the intestine over a predetermined time period.

3. A method as claimed in claim 1 wherein the encapsulated azaribine is administered in an amount sufficient to provide a dosage of from about 1.5 to about 15 grams of azaribine per square meter of animal body surface area per day.

4. A method as claimed in claim 2 wherein the encapsulated azaribine is administered in an amount sufficient to provide a dosage of about 4.5 grams of azaribine per square meter of animal body surface area per day.

5. A method as claimed in claim 1 wherein the azaribine is encapsulated in a film-forming substance comprising a compound selected from the group consisting of alkyl and hydroxyalkyl celluloses and their aliphatic esters, carboxyalkyl celluloses and their salts, cellulose acetate phthalate, polycarboxymethylene and its salts and derivatives, polyvinylalcohol and its esters, polycarboxymethylene copolymer with sodium formaldehyde carboxylate, acrylic polymers and copolyers, edible oils, polyvinylpyrrolidone, polyethyleneglycol and its esters, shellac, polyvinylacetate esters, alkyleneglycolether esters of copolymers of partial ethylene glycol monomethylether ester of ethylacrylate-maleic anhydride copolymer and diethyleneglycol monomethylether ester of methylacrylate-maleic anhydride copolymer, N-butylacrylate-maleic anhydride copolymer, isobutylacrylate-maleic anhydride copolymer and ethylacrylate-maleic anhydride copolymer; polyarginene and polylysine, and mixtures thereof.

6. A method as claimed in claim 5 wherein the azaribine is encapsulated in a film-forming substance comprising cellulose acetate phthalate.

7. A method as claimed in claim 1 further comprising administering to the animal a pyridoxine compound within twenty-four hours before or after the administration of the encapsulated azaribine compound.

8. A method as claimed in claim 7 wherein the pyridoxine compound is administered simultaneously with the encapsulated azaribine compound.

9. A method as claimed in claim 7 wherein the pyridoxine compound is administered in an amount sufficient to provide at least about 0.0005 mole of the pyridoxine compound per mole of azaribine administered.

10. A method as claimed in claim 6 wherein the pyridoxine compound is selected from the group consisting of pyridoxine, pyridoxal phosphate, pyridoxamine, pyridoxamine phosphate, pyridoxal, pyridoxine phosphate pyriodoxine hydrochloride and mixtures thereof.

11. A method as claimed in claim 10 wherein the pyridoxine compound is pyridoxine hydrochloride.

12. A method as claimed in claim 10 wherein the pyridoxine compound is pyridoxal phosphate.

13. A method as claimed in claim 10 wherein the pyridoxine compound is pyridoxamine.

14. A method as claimed in claim 10 wherein the pyridoxine compound is pyridoxamine phosphate.

15. A method as claimed in claim 10 wherein the pyridoxine compound is pyridoxal.

16. A method as claimed in claim 10 wherein the pyridoxine compound is pyridoxine phosphate.

17. A method as claimed in claim 10 wherein the pyridoxine compound is pyridoxine.

18. A method as claimed in claim 1 wherein the azaribine is emulsified in an oil so that the azaribine is selectively absorbed in the intestine.

19. An azaribine-containing composition for oral administration to animals having azaribine-responsive disease and who exhibit severe decrease in serum pyridoxal phosphate levels following the oral administration of azaribine comprising azaribine and an enteric coating encapsulating the azaribine, said enteric coating being selectively soluble in the digestive juice of the intestine.

20. A composition as claimed in claim 19 wherein the enteric coating comprises a compound selected from the group consisting of alkyl and hydroxyalkyl celluloses and their aliphatic esters, carboxyalkyl celluloses and their salts, cellulose acetate phthalate, polycarboxymethylene and its salts and derivatives, polyvinylalcohol and its esters, polycarboxymethylene copolymer with sodium formaldehyde carboxylate, acrylic polymers and copolymers, edible oils, polyvinyl-pyrrolidone, polyethyleneglycol and its esters, shellac, polyvinylacetate esters, alkyleneglycolether esters of copolymers of partial ethylene glycol monomethylether ester of ethylacrylate-maleic anhydride copolymer and diethyleneglycol monomethylether ester of methylacrylate-maleic anhydride copolymer, N-butylacrylate-maleic anhydride copolymer, isobutylacrylate-maleic anhydride copolymer and ethylacrylate-maleic anhydride copolymer; polyarginene and polylysine, and mixtures thereof.

21. A composition as claimed in claim 19 wherein the enteric coating is a time-release coating which dissolves in the digestive juice of the intestine over a predetermined time period.

22. A composition as claimed in claim 19 further comprising a pyridoxine compound.

23. A composition as claimed in claim 22 wherein the pyridoxine compound is present in an amount sufficient to provide at least about 0.0005 mole of pridoxine compound per mole of azaribine in the composition.

24. A composition as claimed in claim 20 wherein the pyridoxine compound is selected from the group consisting of pyridoxine, pyridoxal phosphate, pyridoxamine, pyridoxamine phosphate, pyridoxal, pyridoxine phosphate, pyridoxine hydrochloride and mixtures thereof.

25. A composition as claimed in claim 24 wherein the pryidoxine compound is pyridoxine hydrochloride.

26. A composition as claimed in claim 24 wherein the pyridoxine compound is pyridoxal phosphate.

27. A composition as claimed in claim 24 wherein the pyridoxine compound is pyridoxamine.

28. A composition as claimed in claim 24 wherein the pyridoxine compound is pyridoxamine phosphate.

29. A composition as claimed in claim 24 wherein the pyridoxine compound is pyridoxal.

30. A composition as claimed in claim 24 wherein the pyridoxine compound is pyridoxine phosphate.

31. A composition as claimed in claim 24 wherein the pyridoxine compound is pyridoxine.

32. A composition as claimed in claim 19 wherein the azaribine is emulsified in an oil so that the azaribine is resistant to absorption in the stomach.

* * * * *

UNITED STATES PATENT AND TRADEMARK OFFICE
CERTIFICATE OF CORRECTION

PATENT NO. : 5,023,083
DATED : June 11, 1991
INVENTOR(S) : William Drell

It is certified that error appears in the above-identified patent and that said Letters Patent is hereby corrected as shown below:

On the title page:

[54] Title, change "AZARBINE" to -- AZARIBINE --.

Column 1, line 2, change "AZARBINE" to -- AZARIBINE --.
Column 2, line 53, change "tO" to -- to --.
Column 2, line 64, change "hydroxybutylmethyl-cellulose" to
    -- hydroxybutylmethylcellulose --.
Column 3, lines 10,11, change "polyvinyacetate" to
    -- polyvinylacetate --.
Column 4, line 14, change "azarbine" to -- azaribine --.
Column 4, line 26, after "about" insert -- 1 --.
Column 4, line 29, change "blood stream" to
    -- bloodstream --.
Column 4, line 34, after "of" delete "a".
Column 5, line 26, change "nupariel" to -- nu-pariel --.

Signed and Sealed this

Twenty-third Day of March, 1993

Attest:

STEPHEN G. KUNIN

*Attesting Officer*    *Acting Commissioner of Patents and Trademarks*